United States Patent
Dufour et al.

(10) Patent No.: US 10,631,829 B2
(45) Date of Patent: Apr. 28, 2020

(54) SEGMENTATION OF LARGE OBJECTS FROM MULTIPLE THREE-DIMENSIONAL VIEWS

(71) Applicant: KONINKLIJKE PHILIPS N.V., Eindhoven (NL)

(72) Inventors: Cecile Dufour, Eindhoven (NL); Raphael Manua Michel Prevost, Eindhoven (NL); Benoit Jean-Dominique Bertrand Maurice Mory, Eindhoven (NL); Roberto Jose Ardon, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 576 days.

(21) Appl. No.: 14/770,483

(22) PCT Filed: Feb. 27, 2014

(86) PCT No.: PCT/IB2014/059286
§ 371 (c)(1),
(2) Date: Aug. 26, 2015

(87) PCT Pub. No.: WO2014/132209
PCT Pub. Date: Sep. 4, 2014

(65) Prior Publication Data
US 2016/0007970 A1  Jan. 14, 2016

(30) Foreign Application Priority Data
Feb. 28, 2013 (EP) .................................. 13305228

(51) Int. Cl.
*A61B 8/08* (2006.01)
*G06T 7/30* (2017.01)
(Continued)

(52) U.S. Cl.
CPC .............. *A61B 8/523* (2013.01); *A61B 8/085* (2013.01); *A61B 8/13* (2013.01); *A61B 8/4245* (2013.01);
(Continued)

(58) Field of Classification Search
CPC .......... G06T 7/149; G06T 7/30; A61B 8/523; A61B 8/461; A61B 8/5261; A61B 8/5207;
(Continued)

(56) References Cited

U.S. PATENT DOCUMENTS 5,633,951 A   5/1997 Moshbeghi
6,236,875 B1  5/2001 Bucholz et al.
(Continued)

FOREIGN PATENT DOCUMENTS

WO   WO2012117381 A1 * 9/2012 ............. A61B 19/00

OTHER PUBLICATIONS

Faucheux et al "Texture-Based Graph Regularization Process for 2D and 3D Ultrasound Image Segmentation." 19th IEEE International Conference on Image Processing, pp. 2333-2336. (Year: 2012).*

(Continued)

*Primary Examiner* — Angela M Hoffa

(57) ABSTRACT

The present invention relates to an ultrasound imaging system (10) for inspecting an object (33) in a volume (32). The ultrasound imaging system comprises an ultrasound image acquisition probe (14) for acquiring three-dimensional ultrasound images and providing three-dimensional ultrasound image data, comprising a tracking device (25, 27) for tracking a position of the ultrasound image acquisition probe (14) and providing a viewpoint position (128, 130) of the three-dimensional ultrasound images. By this, an improved initialization and improved co-registration and co-segmentation is enabled by providing a plurality of three-dimensional ultrasound images and their respective viewpoint positions (128, 130), and to conduct a segmentation (80) of the object (33) simultaneously out of the plurality of three-dimensional ultrasound images and taking into account the viewpoint positions (128, 130).

17 Claims, 10 Drawing Sheets

(51) Int. Cl.
*G06T 7/149* (2017.01)
*A61B 8/00* (2006.01)
*A61B 8/13* (2006.01)
*A61B 6/00* (2006.01)

(52) U.S. Cl.
CPC .......... *A61B 8/4254* (2013.01); *A61B 8/4263* (2013.01); *A61B 8/461* (2013.01); *A61B 8/467* (2013.01); *A61B 8/483* (2013.01); *A61B 8/5207* (2013.01); *A61B 8/5238* (2013.01); *A61B 8/5261* (2013.01); *A61B 8/58* (2013.01); *G06T 7/149* (2017.01); *G06T 7/30* (2017.01); *A61B 6/5247* (2013.01); *A61B 8/5223* (2013.01); *G06T 2207/10136* (2013.01); *G06T 2207/30048* (2013.01)

(58) Field of Classification Search
CPC .. A61B 8/467; A61B 8/13; A61B 8/58; A61B 8/4263; A61B 8/4254; A61B 8/4245; A61B 8/5238; A61B 8/483; A61B 8/085
See application file for complete search history.

(56) References Cited

U.S. PATENT DOCUMENTS

| | | | | |
|---|---|---|---|---|
| 6,733,458 | B1* | 5/2004 | Steins | A61B 8/0833 600/461 |
| 8,509,506 | B2* | 8/2013 | Ciofolo | G06T 7/149 382/128 |
| 8,520,932 | B2* | 8/2013 | Cool | G06T 17/10 382/128 |
| 8,622,915 | B2* | 1/2014 | Dala-Krishna | A61B 8/0883 600/437 |
| 9,107,631 | B2* | 8/2015 | Shibata | A61B 8/0833 |
| 9,147,258 | B2* | 9/2015 | Thiruvenkadam | G06T 7/0097 |
| 9,697,634 | B2* | 7/2017 | Dala-Krishna | G06T 13/20 |
| 2005/0137477 | A1 | 6/2005 | Kockro | |
| 2008/0139938 | A1 | 6/2008 | Yang et al. | |
| 2009/0018445 | A1 | 1/2009 | Schers et al. | |
| 2009/0069684 | A1 | 3/2009 | Shibata et al. | |
| 2012/0027278 | A1 | 2/2012 | Chaney et al. | |
| 2012/0041722 | A1 | 2/2012 | Quan et al. | |
| 2012/0250933 | A1 | 10/2012 | Porikli et al. | |
| 2014/0193053 | A1* | 7/2014 | Kadoury | G06T 11/008 382/131 |
| 2015/0213613 | A1* | 7/2015 | Prevost | G06T 7/0097 382/131 |
| 2017/0181730 | A1* | 6/2017 | Ardon | A61B 8/5246 |
| 2017/0196540 | A1* | 7/2017 | Dufour | A61B 8/5215 |

OTHER PUBLICATIONS

Treece et al, "3D Ultrasound Measurement of Large Organ Volume" Medical Image Analysis 5 (2001) p. 41-54.

Lelieveldt et al, "Mutli-View Active Appearance Models for Consistent Segmentation of Multiple Standard Views:Application to Long-And Short Axis Cardiac MR Images" International Congress Series 1256 (2003) p. 1141-1146.

Hussein et al, "Crosstrack: Robust 3D Tracking From Two Cross Sectional Views" IEEE Conference on Computer Vision and Pattern Recognition, Jun. 20-25, 2011.

Jawarneh et al, "Automatic Initialization of Contour for Level Set Algorithms Guided by Intergration of Multiple.." Second International Conference of Computational Intelligence, Sep. 28-30, 2010 p. 315-520.

Yezzi et al "A Variational Framework for Integrating Segmentation of Registration Through Active Contours" Medical Image Analysis vol. 7, No. 2, Jun. 2, 2003, p. 171-185.

Mory et al "Real-Time 3D Image Segmentation by User-Constrained Template Deformation" Proceedings of MICCA Jan. 2012.

* cited by examiner

SEGMENTATION OF LARGE OBJECTS FROM MULTIPLE THREE-DIMENSIONAL VIEWS

This application is the U.S. National Phase application under 35 U.S.C. § 371 of International Application No. PCT/IB2014/059286, filed on Feb. 27, 2014, which claims the benefit of EP Application No. 13305228.2 filed on Feb. 28, 2013. These applications are hereby incorporated by reference herein.

FIELD OF THE INVENTION

The present invention relates to three-dimensional ultrasound imaging. In particular, the current invention relates to image processing and the segmentation of objects in a scanned volume.

BACKGROUND OF THE INVENTION

In three-dimensional ultrasound imaging, or volume imaging, the acquisition of a three-dimensional image can be performed differently according to the probe. For instance, using an xMatrix probe, for example the X6-1 of Philips, a genuine 3D acquisition can be performed. Using a mechanical probe, for example the V6-2 of Philips, the 3D volume is obtained from the acquisition of multiple two-dimensional slices whose calibration is driven mechanically. Using a two-dimensional probe, a three-dimensional volume is made by conducting many two-dimensional scans that slice through the volume of interest. Hence, a multitude of two-dimensional images is acquired that lie next to another. Further, by proper image processing, a three-dimensional image of the volume of interest can be built out of the multitude of two-dimensional images. In all of the cases listed above, the three-dimensional information is displayed in proper form on a display for the user of the ultrasound system.

Further, so-called live three-dimensional imaging, or 4D imaging, is often used in clinical applications. In live three-dimensional imaging, a real-time view on the volume can be acquired enabling a user to view moving parts of the anatomical site, for example a beating heart or else. In the clinical application of live three-dimensional imaging there is sometimes a need to image a relatively small area of the heart such as a single valve, or a septal defect, and there is sometimes the need to image a large area of the heart such as an entire ventricle.

Two-dimensional image segmentation is a common task for radiologists. Image segmentation of three dimensional objects is often performed from multiple stacked two-dimensional segmentations. Image segmentation in three dimensions is less common. The extracted surface can be used either to quantify the volume of an organ or a tumor, or as a landmark to perform feature-based image registration. However, it is often tedious to manually segment an organ in a 3D image. While quantification and visualization tools are relatively available for 2D images, 3D volumes analysis is often done by hand through tedious procedures difficult to realize in clinical practice. Hence, such methods are quite inconvenient. Automatically conducted and precise segmentations are therefore needed, but difficult to obtain, especially in ultrasound images which are corrupted by a lot of noise and various artifacts.

Document US 2008/0139938 shows a system for acquiring, processing, and presenting boundaries of a cavity-tissue interface within a region-of-interest in an ultrasound image based upon the strength of signals of ultrasound echoes returning from structures within a region-of-interest (ROI). The segmentation of boundaries of cavity shapes occupying the region-of-interest utilizes cost function analysis of pixel sets occupying the cavity-tissue interface. The segmented shapes are further image processed to determine areas and volumes of the organ or structure containing the cavity within the region-of-interest.

Further, ultrasound is a largely used modality, especially during minimally invasive interventions, e.g. in the liver as it is harmless to the patient. Ultrasound images do not provide the same medical information compared to e.g. the computer tomography (CT) or magnetic resonance (MR) modality. All these modalities complement each other in providing comprehensive inside-body views. However, ultrasounds can have issue visualizing in between the ribs, as the ribs cast a shadow masking information. Also, ultrasound images have a limited field of view compared to computer tomography or magnetic resonance tomography. It has become a topic to align computer tomography or magnetic resonance tomography data of an object within a human body with ultrasound image data. CT or MR are usually acquired prior to the use of ultrasound and contain precise information about e.g. a tumor shape and location. During the use of ultrasound imaging, it is desired to keep at all times the annotated data, e.g. tumor shape and location acquired via CT and/or MR, aligned with the ultrasound data.

Further, even if no further modalities are used, ultrasound images might be acquired from different viewpoints. Hence, it is a further topic to register multiple ultrasound images towards each other.

There is a need for improved automatic or at least computer-aided segmentation and registration tools.

SUMMARY OF THE INVENTION

It is an object of the invention to provide an ultrasound imaging system for inspecting an object in a volume that is more convenient to calibrate and is able to display segmented ultrasound images registered to each other or any alternative reference, for example, an image taken via a different modality.

In a first aspect of the present invention, an ultrasound imaging system for inspecting an object in a volume is presented that comprises an ultrasound image acquisition probe for acquiring three dimensional ultrasound images and providing or outputting three dimensional ultrasound image data, comprising a tracking device for tracking a position of the ultrasound image acquisition probe and providing a viewpoint position of the three dimensional ultrasound images and an image processor configured to receive the three dimensional ultrasound image data and to provide display data wherein the image processor is configured to receive a plurality of three dimensional ultrasound images and their respective viewpoint positions, and to conduct a segmentation of the objects simultaneously out of the plurality of three dimensional ultrasound images.

In a further aspect of the present invention, it is presented a method for providing an ultrasound image of an object in a volume, when the method comprises the steps of providing, in particular acquiring, ultrasound image data of the volume comprising a plurality of three dimensional ultrasound images and viewpoint positions of each three dimensional ultrasound images, processing the ultrasound image data to segment and register the objects simultaneously out of a first ultrasound image and at least one further ultrasound image to provide segmented and registered ultrasound image data, and displaying an ultrasound image based on the segmented and registered ultrasound image data.

In a further aspect of the present invention, a computer program is presented comprising program code means for causing a computer to carry on steps of the method for providing an ultrasound image of an object in a volume, the method comprising the steps of providing, in particular acquiring, ultrasound image data of the volume comprising a plurality of three dimensional ultrasound images and viewpoint positions of each ultrasound image, processing the ultrasound image data to segment and register the objects simultaneously out of a first ultrasound image and at least one further ultrasound image to provide segmented and registered ultrasound image data, and displaying an ultrasound image based on the segmented and registered ultrasound image data, when said computer program is carried out in a computer.

It is a basic idea of the invention to use a tracking device, in particular an electromagnetic tracking device, to facilitate registration and co-segmentation of the ultrasound images. Via the viewpoint positions associated with each ultrasound image, and tracked with the tracking device, it is possible to roughly initialize a registration search space. Further exact results found via the co-segmentation and registration may be used to accurately calibrate the tracking device.

By this, it is further facilitated to keep the ultrasound images registered with a previously acquired three dimensional image of the same volume, for example a computer tomography (CT) image or a magnetic resonance (MR) image aligned with the ultrasound data. To enable this, a tracking device is attached to the ultrasound image acquisition probe, acting as a kind of global positioning system (GPS) for the ultrasound view. Once the tracking device is calibrated, especially against a reference, for example, a CT volume, a subsequent ultrasound volume acquisition is aligned with the CT volume.

A calibration of the tracking device, in particular an electromagnetic tracking device can be generally made from different ways, for example, fiducials located on a chest of the patient can be used. Further, a manual registration locating salient features (landmarks) in the CT or MR views in the ultrasound views may be used. Of course, imaged processing based techniques, which automatically identify either landmarks (for example liver vessels) present in both the CT and ultrasound views or shape surfaces, may be used to align the images. However, in addition to this, the current invention suggests further calibration processes.

This is as landmarks, like liver vessels, cannot always be visualized in the CT data if no contrast injection is made. Hence, landmark techniques are given some constraints on the CT data. A registration using fiducials placed, for example, on the chest of the patient, cannot always be implemented for various reasons. For instance, this kind of registration and calibration requires fiducials to stay in place during these CT scan and during a further ultrasound acquisition. However, this puts constraints on the time between the CT image acquisition (or MR image acquisition) and the acquisition of the ultrasound imaging system. Further, some objects or organs may be too large to be captured entirely using ultrasound image acquisition probes. Then, matching a subset of the respective organ may not provide accurate registration on the entire surface. Also, an ultrasound volume may be severely impaired because of shadow effects inherent to echography. Further, also a segmentation of an organ such as the liver may be extracted from, for example, CT data very accurately. However, this result may not necessarily match the respective shape and volume of the patient at the time of an ultrasound acquisition. The patient may have changed his or her pose and/or the patient may present a respiratory phase different than during the CT acquisition. However, with the ultrasound image acquisition device according to the current invention, the solution for the segmentation and accurate registration itself can be provided being robust to ultrasound artifacts and being very accurate. Further, the proposed invention copes with different patient poses and respiratory phases. Last, large organs like the liver may also be dealt with conveniently.

Hence, essentially, the current invention suggests a position tracking system, for example, an electromagnetic (EM) tracking device attached to the ultrasound acquisition probe. The data from the tracking device is processed and taken into account by the image processor when processing the image data provided by the ultrasound image acquisition probe. Hence, an acquisition of a plurality of ultrasound images with different viewpoint position that is also recorded by the tracking device can be processed by the ultrasound image acquisition system. The segmentation of the object and the registration of the plurality of ultrasound images can be conducted via a model-based registration and co-segmentation process.

Preferred embodiments of the invention are defined in the dependent claims. It shall be understood that the claimed method has similar and/or identical preferred embodiments as the claimed device and as defined in the dependent claims.

In an embodiment of the ultrasound imaging system, the image processor is configured to conduct the segmentation by minimizing an energy term so that a deformed initial geometric shape matches the object's boundary as good as possible.

It has been found that a model-based method using a previously specified initial geometric shape that is transformed during the segmentation process provides a robust converging method to find and segment the object in all ultrasound images simultaneously. As will be explained in further detail below, the segmentation comprises deforming an initial model, for example an initial model that roughly represents the shape of the target object. In a further embodiment, the energy term comprises a first term representing a first three dimensional ultrasound image and at least one further representing a further three dimensional ultrasound image, wherein the deformed initial geometric shape is the same both in the first and the at least one further term, and wherein data fidelity terms or at least one of the first and the at least one further term each comprises a registering transformation registering the three dimensional ultrasound image and the at least one three dimensional ultrasound image.

The first and the at least one further ultrasound image may be registered to a common reference. The common reference may be, for example, one of the ultrasound images, for example, the first ultrasound image or possibly a three dimensional image acquired via a different modality, for example via CT or MR. Of course, the common reference may also be any position within a common coordinate system. Important is to finally know all positions relative to each other. By this, when segmenting the object out of the three dimensional ultrasound image data, at the same time the registering transformation can be found. There is no need to pre-register accurately the three dimensional ultrasound image data and the at least one further three dimensional ultrasound image data prior to the segmentation. Rather, the registration of the at least two image data sets is performed simultaneously to the segmentation. The geometric transformation that aligns them is therefore available as a side outcome. This enables to register the plurality of three dimensional ultrasound image data and to provide registered images of the ultrasound imaging system simultaneously.

In a further embodiment, a deformation of the initial geometric shape is conducted by applying a global transformation and a non-rigid local transformation on the initial geometric shape, in particular wherein the global transformation translates, rotates and scales the initial geometric shape, and wherein the non-rigid local transformation applies a displacement field on the initial geometric shape.

In particular, the displacement field may have a build in smoothness. Further, the energy term may further comprise a third term constraining the non-rigid local transformation. This construction of the energy term provides for the advantage that deforming the initial geometric shape that roughly corresponds to the object to be segmented, may not be deformed too much during transformation. This is achieved by separating the deformation of the initial geometric shape into a global transformation translating and rotating and scaling the initial geometric shape and a separate local transformation that deforms the initial geometric shape. By this, the method can further apply a third term penalizing the local transformation so that the shape of the object does not deviate too much from the initial geometric shape. By this, segmentations which are close to the initial geometric shape are favored by the process.

In a further embodiment, the image processor is configured to determine the initial geometric shape based on a segmentation of the object in three dimensional image data acquired via a different modality, for example, computer tomography.

By this, a different modality, for example, CT may be used to accurately find and segment the object, in particular, if it is large, and to use this segmented shape as an initial geometric shape during ultrasound segmentation and registration.

In a further embodiment, the image processor is configured to receive the initial geometric shape as a definition by a user.

Hence, not to be provided for that a user sets a basic geometric former initial geometric shape, for example an ellipsoid or sphere in case to be segmented is a liver. Of course, other basic geometric forms, like cylinders or mean shapes (e.g. the mean shape of the liver) may also be used.

In a further embodiment, the image processor is configured to determine the registration transformation for each three dimensional ultrasound image to a common reference, for example three dimensional image data acquired via a different modality or one of the plurality of three dimensional ultrasound images.

By this, for example during an intervention under the control of the ultrasound image acquisition system, registered images can be presented to a user, for example with a side-by-side view on the object acquired via a different modality, for example CT or MR.

In a further embodiment, the image processor is further configured to conduct the segmentation based on an initialization of the registration search space, wherein the initialization of the registration search space is conducted by roughly positioning an initial geometric shape in each of the three dimensional ultrasound images by minimizing an energy term so that the initial geometric shape matches an object boundary within the three dimensional ultrasound image as good as possible.

By this initialization, the search space for the registration can be significantly reduced. As a rough estimation not only of the initial geometric shape of the object but also the viewpoint position from which the ultrasound image was acquired can be delivered. Optimization of the energy term is searched only around these initial positions.

In a further embodiment, the energy term is minimized by optimizing merely a three dimensional translation transformation and taking into account a viewpoint position of the ultrasound image acquisition probe when acquiring a respective three dimensional image, and wherein a calibration of the three dimensional orientation of the image acquisition probe tracked by the tracking device is taken into account.

By this, a pre-calibration workflow might first be conducted to provide an initial positioning information. For instance, it consists in the acquisition and recording of two tracking positions via the electromagnetic (EM) tracking device, roughly positioned on the sternum of the patient and giving clue on the cranio-caudal axis of the patient. Then an automatic initialization of the registration search space can be conducted based on the knowledge of this pre-calibration workflow.

By this, the initialization is conveniently speeded up. As only a translation transformation is to be searched for as the viewpoint positions acquired with a tracking device may be taken into account, the initialization may be acquired very fast. Further, when dealing with only partly acquired objects, the co-segmentation and registration may be initialized in a very robust way.

In a further embodiment, the ultrasound imaging system is further configured to provide for a request refinement of the segmentation and registering transformation by using another plurality of the three dimensional ultrasound images acquired via the ultrasound image acquisition probe and the already conducted initialization.

During the refinement, an acquisition of at least one ultrasound volume of the object is taken. Then, again a segmentation and localization of the ultrasound images is conducted based on the model-based registration and co-segmentation process. However, the previously conducted initialization is used.

In a further embodiment, the ultrasound imaging system comprises tracking device that is an electromagnetic tracking device.

By this, electromagnetic navigation and tracking technology may be used that has no side requirements and uses very small sized sensors that are particularly useful for integrating in small devices like probes.

In a further embodiment of the method, the method comprises the further step of providing, in particular acquiring, a three dimensional image of the object of the volume acquired using a different modality prior to the step of providing ultrasound image data as input.

As already explained above, the three dimensional image of the object acquired using a different modality may be used to segment the object, in particular in case of a very large object, in full out of the image acquired using the different modality to acquire the initial geometric shape and used to initialize the segmentation process in the ultrasound images.

In a further embodiment, the method comprises the first step of calibrating a tracking device for acquiring the viewpoint positions by moving the image acquisition probe to at least two different locations on a known axis or orienting the probe in a predefined relationship, i.e. parallel or perpendicular, to a known axis, for example to cranio-caudal axis of a patient.

In a particular embodiment, the current invention may be used with an electromagnetic tracking device and during a minimally invasive intervention. Hence, an echography system or ultrasound system equipped with a locating sensor benefits from this particular invention. The current invention may be used in a system wherein the shape of the object is actually known from a previously conducted segmentation in images acquired for a different modality. However, the invention also addresses the co-registration and segmentation of a target object to which a rough estimate of the shape of the object is given, for example just a sphere or a mean shape. Still the invention finds the application also in ultrasound systems only, that are equipped with a tracking device and for which, however, no CT or MR is available. For this application, the invention serves to segment of the object within multiple ultrasound images with different viewpoint positions.

In a further embodiment, the image processor is further configured in that the registering transformation is affine.

Generally, the registering transformation applied in one of the first and second terms of the energy term or, in other words, the data similarity terms of the energy can berigid transformations or non-rigid transformations. The registration transformation might be any kind of global linear transformation. In particular, it can be an affine transformation. An affine transformation is a transformation which preserves straight lines and ratios of distances between points lying on a straight line. An affine transformation is equivalent to a linear transformation followed by a translation. In particular, the affine transformation may be a linear transformation with up to twelve parameters.

However, it has to be emphasized that the suggested system and methods also can be applied to the inspection of any other organ of a patient or object within a patient. Other suitable basic geometrical shapes might also be found for the spleen, the bowel, the pancreas, the liver or a heart of a patient. Further, the aorta may be an object which might be inspected via the suggested systems and methods. For an aorta, an elongated cylinder may be the basic geometrical shape.

In a further embodiment, the ultrasound imaging system further comprises a transducer array configured providing an ultrasound receive signal, a beam former configured to control the transducer array to scan the volume, and further configured to receive the ultrasound receive signal and to provide an image signal, a controller for controlling the beam former, and a signal processor configured to receive the image signal and to provide three-dimensional image data and contrast-enhanced three-dimensional image data.

By this, a fully functioning ultrasound imaging system capable to acquire multiple three-dimensional images and to provide it to the image processor and providing it to the image processor is provided. The contrast-enhanced three-dimensional image data may then be used as data of a different modality to support segmentation and registration.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
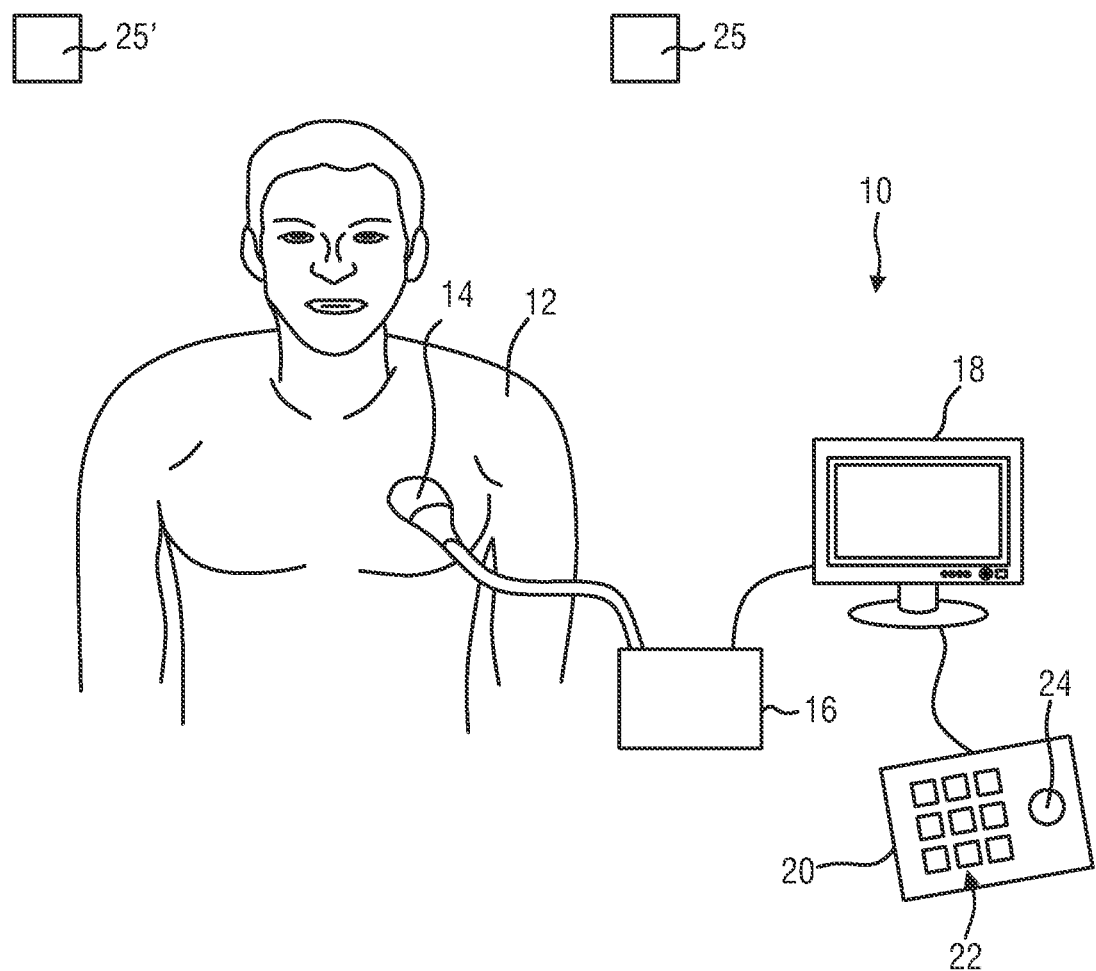
FIG. 1 shows a general overview of an ultrasound image system.

FIG. 1 shows a schematic illustration of an ultrasound system 10 according to an embodiment, in particular a medical ultrasound three-dimensional imaging system. The ultrasound imaging system 10 is applied to inspect a volume of an anatomical site, in particular an anatomical site of a patient 12. The ultrasound system 10 comprises an ultrasound image acquisition probe 14 having at least one transducer array having a multitude of transducer elements for transmitting and/or receiving ultrasound waves. In one example, the transducer elements each can transmit ultrasound waves in form of at least one transmit impulse of a specific pulse duration, in particular a plurality of subsequent transmit pulses. The transducer elements can for example be arranged in a one-dimensional row, for example for providing a two-dimensional image that can be moved or swiveled around an axis mechanically. Further, the transducer elements may be arranged in a two-dimensional array, in particular for providing a multi-planar or three-dimensional image.

In general, the multitude of two-dimensional images, each along a specific acoustic line or scanning line, in particular scanning receive line, may be obtained in three different ways. First, the user might achieve the multitude of images via manual scanning. In this case, the ultrasound image acquisition probe may comprise position-sensing devices that can keep track of a location and orientation of the scan lines or scan planes. However, this is currently not contemplated. Second, the transducer may be automatically mechanically scanned within the ultrasound image acquisition probe. This may be the case if a one dimensional transducer array is used. Third, and preferably, a phased two-dimensional array of transducers is located within the ultrasound image acquisition probe and the ultrasound beams are electronically scanned. The ultrasound image acquisition probe may be hand-held by the user of the system, for example medical staff or a doctor. The ultrasound image acquisition probe 14 is applied to the body of the patient 12 so that an image of an anatomical site in the patient 12 is provided.

Further, the ultrasound system 10 has a controlling unit 16 that controls the provision of a three-dimensional image via the ultrasound system 10. As will be explained in further detail below, the controlling unit 16 controls not only the acquisition of data via the transducer array of the ultrasound image acquisition probe 14 but also signal and image processing that form the three-dimensional images out of the echoes of the ultrasound beams received by the transducer array of the ultrasound image acquisition probe 14.

The ultrasound system 10 further comprises a display 18 for displaying the three-dimensional images to the user.

Further, an input device 20 is provided that may comprise keys or a keyboard 22 and further input devices, for example a track ball 24. The input device 20 might be connected to the display 18 or directly to the controlling unit 16.

Further, the ultrasound system 10 comprises a tracking device, for example an electromagnetic tracking device. Parts of the tracking device are situated within the probe 14 or may be associated with the probe via a clip. Further parts 25, 25', for example sensors like magnetoresistive sensors, may be placed in the circumference of the ultrasound system. Preferably, the spatial coordinates of the further parts 25, 25' are known.

Figure 2:
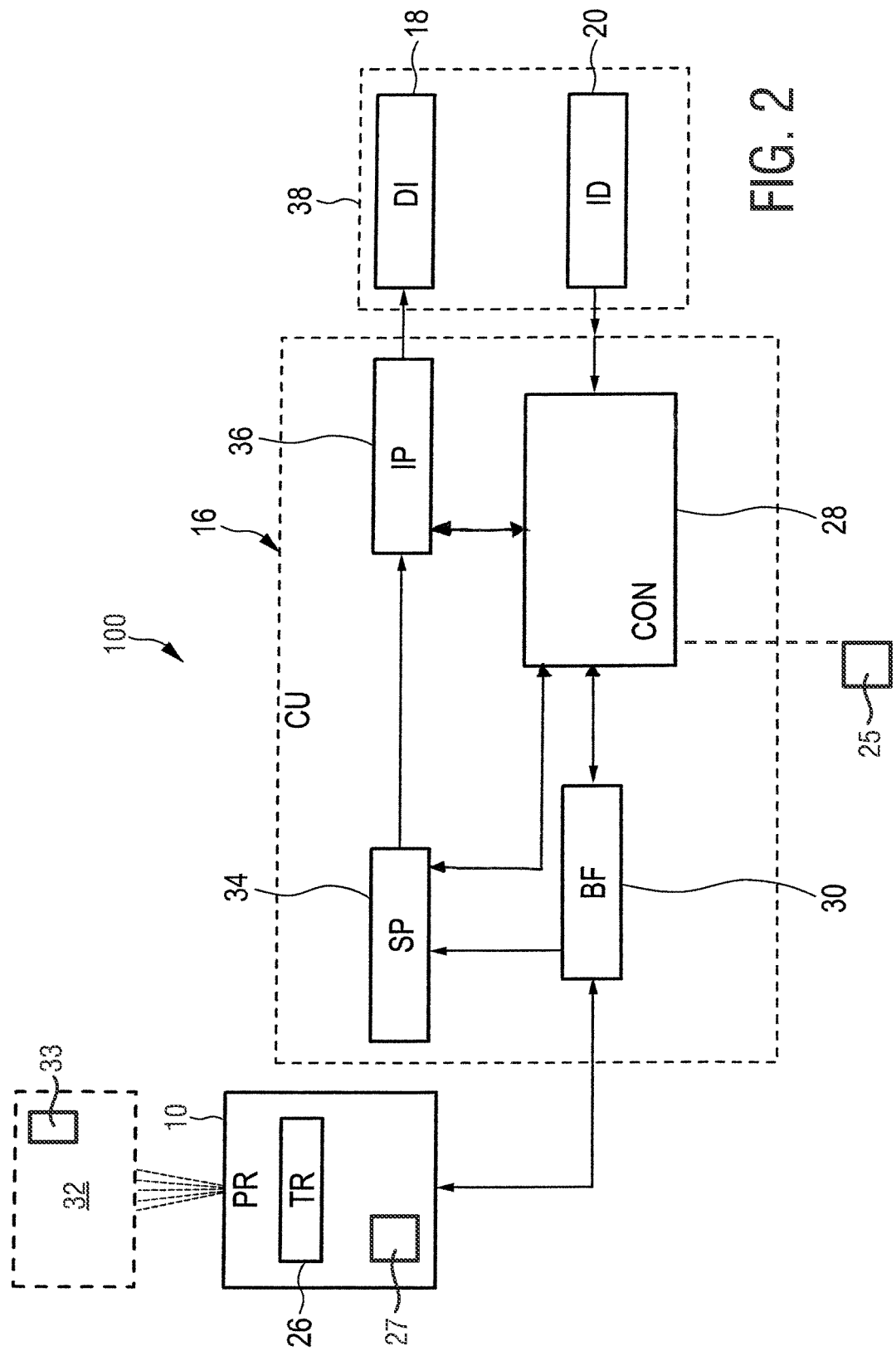
FIG. 2 shows a block diagram showing the essential elements of the ultrasound system.

FIG. 2 shows a schematic block diagram of the ultrasound system 10. As already laid out above, the ultrasound system 10 comprises an ultrasound image acquisition probe (PR) 14, the controlling unit (CU) 16, the display (DI) 18 and the input device (ID) 20. As further laid out above, the probe (PR) 14 comprises a transducer array 26, for example a phased two-dimensional transducer array or automatically scanned one-dimensional transducer array. Further, the probe comprises a part 27 of the tracking device, for example a coil that generates an electromagnetic field that is sensed via the sensors 25, 25'. In general, the controlling unit (CU) 16 may comprise a central processing unit that may include analog and/or digital electronic circuits, a processor, microprocessor or the like to coordinate the whole image acquisition and provision. Further, the controlling unit 16 comprises a herein called central processing unit 28. However, it has to be understood that the central processing unit 28 does not need to be a separate entity or unit within the ultrasound system 10. It can be a part of the controlling unit 16 and generally be hardware or software implemented. The current distinction is made for illustrative purposes only. The central processing unit (CPU) 28 as part of the controlling unit 16 may control a beam former and, by this, what images of the volume 32 are taken and how these images are taken. The beam former (BF) 30 generates the voltages that drives the transducer array (TR) 26, determines parts repetition frequencies, it may scan, focus and apodize the transmitted beam and the reception or receive beam(s) and may further amplify filter and digitize the echo voltage stream returned by the transducer array 26. Further, the central processing unit 28 of the controlling unit 16 may determine general scanning strategies. Such general strategies may include a desired volume acquisition rate, lateral extent of the volume, an elevation extent of the volume, maximum and minimum line densities, scanning line times and the line density as already explained above. The beam former 30 further receives the ultrasound signals from the transducer array 26 and forwards them as image signals.

Further, the ultrasound system 10 comprises a signal processor (SP) 34 that receives the image signals. The signal processor 34 is generally provided for analogue-to-digital-converting, digital filtering, for example, band pass filtering, as well as the detection and compression, for example a dynamic range reduction, of the received ultrasound echoes or image signals. The signal processor forwards image data.

Further, the ultrasound system 10 comprises an image processor (IP) 36 that converts image data received from the signal processor 34 into display data finally shown on the display 18. In particular, the image processor 36 receives the image data, preprocesses the image data and may store it in an image memory. These image data is then further post-processed to provide images most convenient to the user via the display 18. In the current case, in particular, the image processor 36 may form the three-dimensional images out of a multitude of two-dimensional images in each slice.

A user interface is generally depicted with reference numeral 38 and comprises the display 18 and the input device 20. It may also comprise further input devices, for example, a mouse or further buttons which may even be provided on the ultrasound image acquisition probe 14 itself.

A particular example for a three-dimensional ultrasound system which may apply the current invention is the CX32 CompactXtreme Ultrasound system sold by the applicant, in particular together with a X6-1 or X7-2t TEE transducer of the applicant or another transducer using the xMATRIX technology of the applicant. In general, matrix transducer systems as found on Philips iE33 systems or mechanical 3D/4D transducer technology as found, for example, on the Philips iU22 and HD15 systems may apply the current invention.

Figure 3:
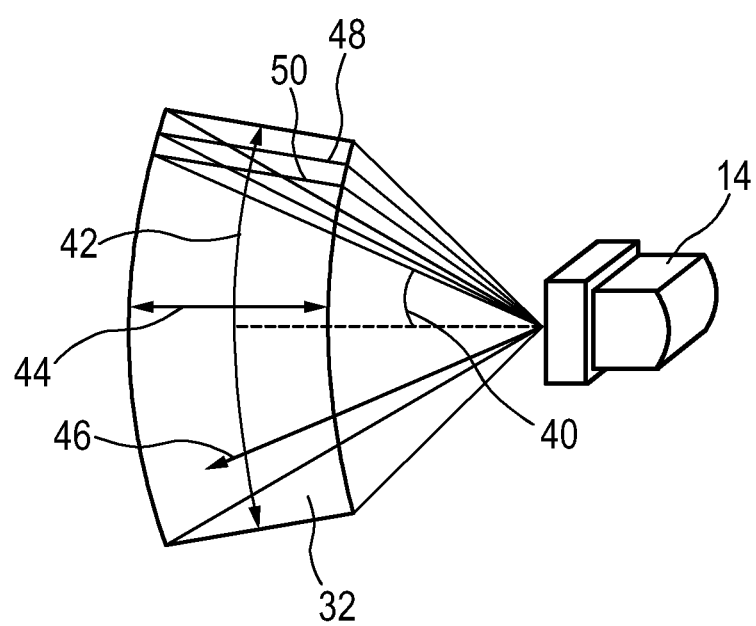
FIG. 3 shows a schematic drawing for explaining the volume of acquisition.

FIG. 3 shows an example of a volume 32 relative to the ultrasound image acquisition probe 14. The exemplary volume 32 depicted in this example is of a sector type, due to the transducer array of the ultrasound image acquisition probe 14 being arranged as a phased two-dimensional electronically scanned array. Hence, the size of the volume 32 may be expressed by an elevation angle 42 and a lateral angle 44. A depth 46 of the volume 32 may be expressed by a so-called line time in seconds per line. That is the scanning time spent to scan a specific scanning line.

The volume 32 may be divided into a multitude of slices 48, 50 or two-dimensional images. Only two slice 48, 50 are depicted for illustrative purposes. Actually, a multitude of slices 48, 50 having different elevational angles 40 are spread over the volume 32. Of course, the slices 48, 50 may also be oriented in the elevational direction and spread across the volume 32 in the lateral direction. During image acquisition, the two-dimensional transducer array of the ultrasound image acquisition probe 14 is operated by a beam former in a way that the volume 32 is scanned along a multitude of these scan lines within each of the slices 48, 50 sequentially. In multi-line receive processing, a single transmit beam might illuminate a multitude, for example four, receive scanning lines along which signals are acquired in parallel. If so, such sets of receive lines are then electronically scanned across the volume 32 sequentially.

In the current application, the target is to segment exactly the same object, e.g. a liver, out of at least two different images. The segmentation comprises deforming an initial model, e.g. an initial model that roughly represents the shape of the target object. As an example, in case that the target object is a liver, the initial shape might be a sphere or a liver mean shape. This shape is represented by an implicit function, i.e. a function $\phi$, defined in the whole space, which is positive inside the shape and negative outside. The shape is then the zero level-set of such a function. The whole implicit function will be deformed by a space transformation $\psi$. In particular, the zero level-set will change and so will the corresponding object. This transformation is decomposed into two transformations of different kinds $$\psi = \mathcal{L} \circ \mathcal{G}:$$

$\mathcal{G}$ is a global transformation that can translate, rotate or rescale the initial shape.

It will basically correct the initial pose of the model.

$\mathcal{L}$ is a local deformation that will actually deform the object so that it matches more precisely the object to segment in the image.

The goal of the method is then to find the best $\mathcal{L}$ and $\mathcal{G}$, using the image I information. This is done by minimizing the following energy:

$$\int H(\phi \circ \mathcal{L} \circ \mathcal{G}(x)) r(x) + \lambda \int \|\mathcal{L}(x) - x\|^2$$

In the first term, also called data fidelity, H is the Heaviside function (H(x)=1 if x>0 and 0 if x<0) which means that the integral is actually only inside the deformed object. r(x) is an image-based function that returns at each point a negative (respectively positive) value if the voxel is likely to be outside (respectively inside) the object of interest. For ambiguous regions, r(x) is set to zero. The second term, is the so called regularization. The second term is the norm between $\mathcal{L}$ and the identity function. The amplitude of the deformation is penalized because the object shape should not deviate too much from the shape prior. It is to be emphasized that this second term is independent from the position and orientation of the object which was the purpose of the decomposition of the transformation. The minimization of such energy is performed using a gradient descent on both $\mathcal{L}$ and $\mathcal{G}$ at the same time.

In a mere example of only two images, and if the two images were already perfectly registered, then the previously described equation can easily be extended by adding another data fidelity term:

$$\int H(\phi \circ \mathcal{L} \circ \mathcal{G}(x)) r_1(x) + \int H(\phi \circ \mathcal{L} \circ \mathcal{G}(x)) r_2(x) + \lambda \int \|\mathcal{L}(x) - x\|^2$$

However, a registered acquisition might only take place if both US images are acquired simultaneously or shortly after another. It is very unlikely that the US images are registered if acquired subsequently. Hence, this is taken into account with another transformation. In general, this transformation might be non-rigid and of any type. However, if an assumption of looking for the same object can be made, this transformation (denoted $\mathcal{G}_{12}$) can be rigid, i.e. it allows a global change of position and orientation but only with the same size. The transformation $\mathcal{G}_{12}$ could also be set to any affine transform, e.g. to take into account volume changes, without loss of computational efficiency. The energy then becomes $$\int H(\phi \circ \mathcal{L} \circ \mathcal{G}(x)) r_1(x) + \int H(\phi \circ \mathcal{L} \circ \mathcal{G}(x)) r_2 \circ \mathcal{G}_{12}(x) + \lambda \int \|\mathcal{L}(x) - x\|^2$$

Basically, it corrects the image information coming from the second term by the transformation $\mathcal{G}_{12}$. In case of more than images, further terms for each image each comprising its own transformation would have to be added.

The third term, that is optional, is constructed as a constraint to the local deformation. It penalizes if the local deformation causes the shape of the object to deviate too much from the initial geometric shape. Hence, as we search for a minimum, in case the first and the second term lead to the same results, the solution transforming the initial geometric shape less than the other solutions will be considered best. The parameter "λ" may be set to determine the relevance of this constraint.

The optimization is performed by gradient descent simultaneously on $\mathcal{L}$, $\mathcal{G}$ and $\mathcal{G}_{12}$. At the end, a segmentation as the zero level-set of the function $\phi \circ \mathcal{L} \circ \mathcal{G}$ is more precise because it used the information of the two images. Further, estimate of the transformation $\mathcal{G}_{12}$ which allows registering the images to each other is achieved.

Figure 4:
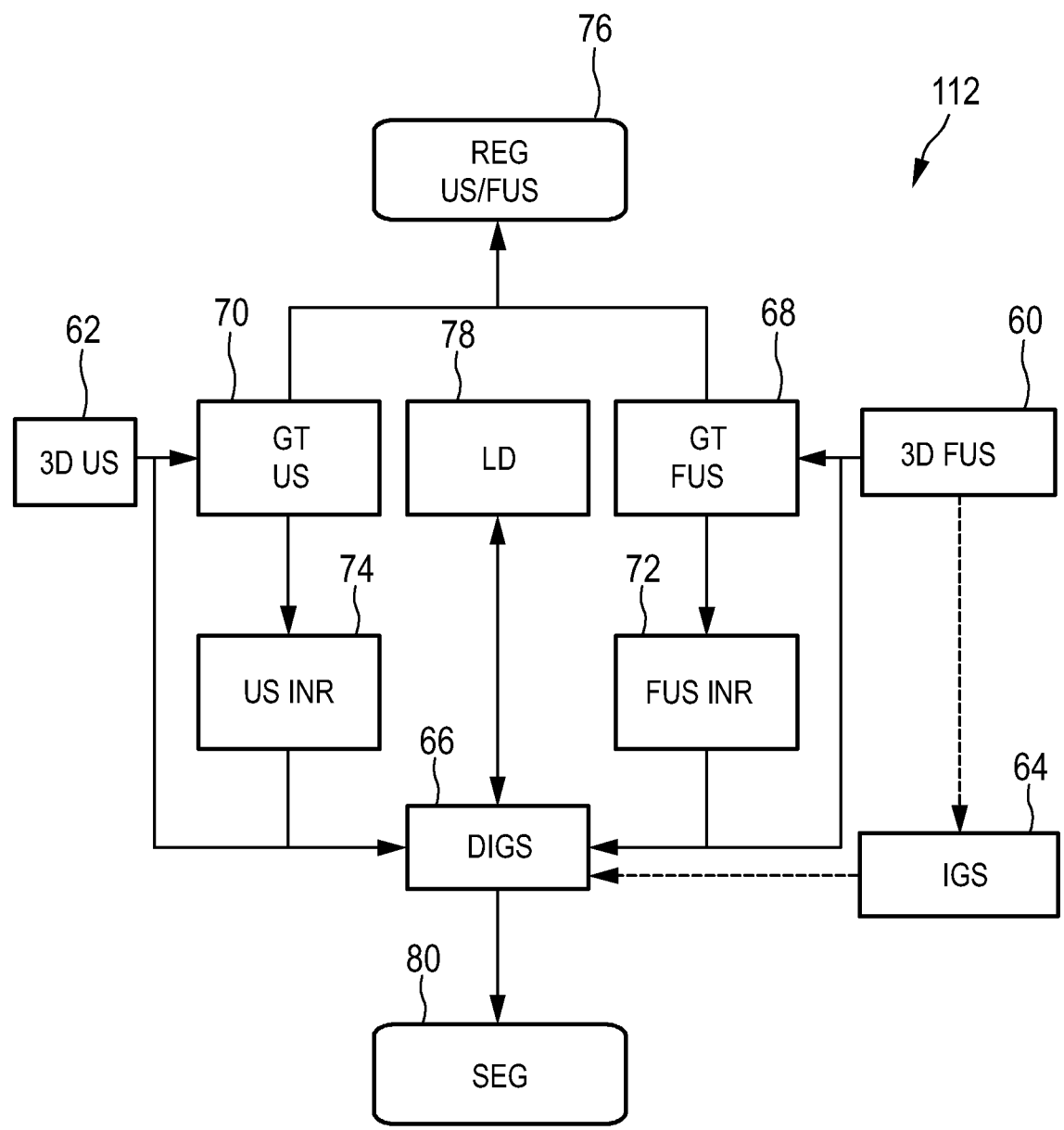
FIG. 4 shows a block diagram to illustrate the co-segmentation and registration process.

FIG. 4 shows an embodiment the segmentation is to be conducted. In this embodiment, also a registration of the three-dimensional ultrasound image data and the further three-dimensional ultrasound image data.

The actual segmentation is obtained by deforming an initial geometric shape with two transformations, a global one that takes into account rotation, translation and scaling and a local one which actually modifies the initial geometric shape. The two transformations are found by minimizing a region competition energy so that the deformed shape matches the target object's boundary in the image data. In this embodiment, two image based terms are used in the energy term so that the plurality of US images is taken into account. In case of more than two ultrasound images, more image based energy terms may be added—one for each image. As the two (or more) image data sets are not necessarily registered, one of the two image-based terms has to be corrected by a transformation. If for example the liver is to be scanned and a patient holds its breath, an assumption can be made that a liver is not deformed during the acquisition of the normal ultrasound image data and the further ultrasound image data so that a rigid transform can be applied only translating and rotating. Then, the energy with respect to the global transform, the local transform and the rigid transform between the US images can be optimized.

At first, the segmentation may be initialized by finding or setting an initial geometric shape 64. This may also be conducted manually. Initializing the registration may be conducted by searching for the initial geometric shape 64 also in the normal three-dimensional ultrasound image data only by translating and rotating the initial geometric shape. By this, an initial geometric transformation between the normal three-dimensional ultrasound image data and the further three-dimensional ultrasound image data can be provided. This geometric transformation may be estimated by an exhaustive search (on translations and rotations) in the normal three-dimensional ultrasound image of the previously estimated initial shape, for example an ellipsoid, a sphere or a cylinder. Further, an initialization may be found via the tracking device as explained in further detail below.

Then, having provided initializations for block 64 and 76 and having provided the three-dimensional ultrasound image data 62 and the further three-dimensional ultrasound image data 60, the actual segmentation can take place. The segmentation works as follows.

The previously set initial geometric shape will now be deformed according to the previously described framework to segment the object or liver more precisely. In the particular application, the image-based term may be set to $r(x) = \pm \Delta I(x)$, where the $\Delta$-operator denotes the Laplacian operator. Mathematically, minimizing the Laplacian of the image inside an object means that the normal vectors of the object's surface should match the image gradient; that is to say, the segmentation method will look for bright-to-dark edges (or dark-to-bright, depending on the multiplying sign).

In FIG. 4, the global transformation of the ultrasound image data 70 and the global transformation of the further ultrasound image data 68 are shown to be conducted transforming the image data of all images into one reference system. The normal three-dimensional ultrasound image data in a block 74 and the further ultrasound image data is transformed in a block 72. However, of course, it may be the case that the coordinate system of either the three-dimensional ultrasound image data or the further ultrasound image data may be used as the referential system so that only one of the normal three-dimensional ultrasound image data and the further three-dimensional ultrasound image data needs to be really transformed. Further, all ultrasound image data may also be transformed to a reference system of previously acquired via a further modality, e.g. magnetic resonance tomography or else. Simultaneously, a local deformation 78 is conducted as explained above. This leads to the deformed model of 66 of the initial geometric shape 64 as explained above. By applying this deformed model of the initial geometric shape, the object can be segmented out of the normal three-dimensional ultrasound image data and the further three-dimensional ultrasound image data in block 80. As a side outcome, as the normal three-dimensional ultrasound image data and the further three-dimensional ultrasound image data have to be globally and locally deformed in the same reference system, a transformation registering the normal three-dimensional ultrasound image data and the three-dimensional ultrasound image data is found as block 76.

Figure 5A:
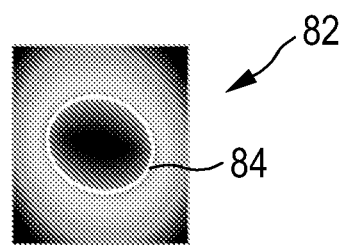
FIGS. 5*a* to 5*c* show examples to explain the transformations conducted on an initial geometric shape during the segmentation.

Again, for illustrative purposes, FIG. 5a shows the example function ϕ 84 in an image 82.

Figure 5B:
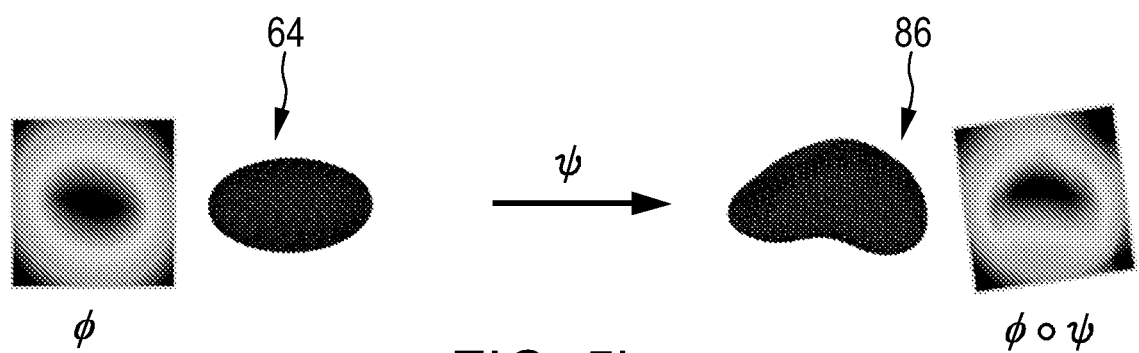

In FIG. 5b, it is shown that the initial geometric shape 64 found in the initialization process explained above out of the basic geometric shape 84 is provided. A transformation ψ is searched for that leads to a deformed model 86 that segments the object out of the normal three-dimensional ultrasound image data and the further three-dimensional ultrasound image data.

Figure 5C:
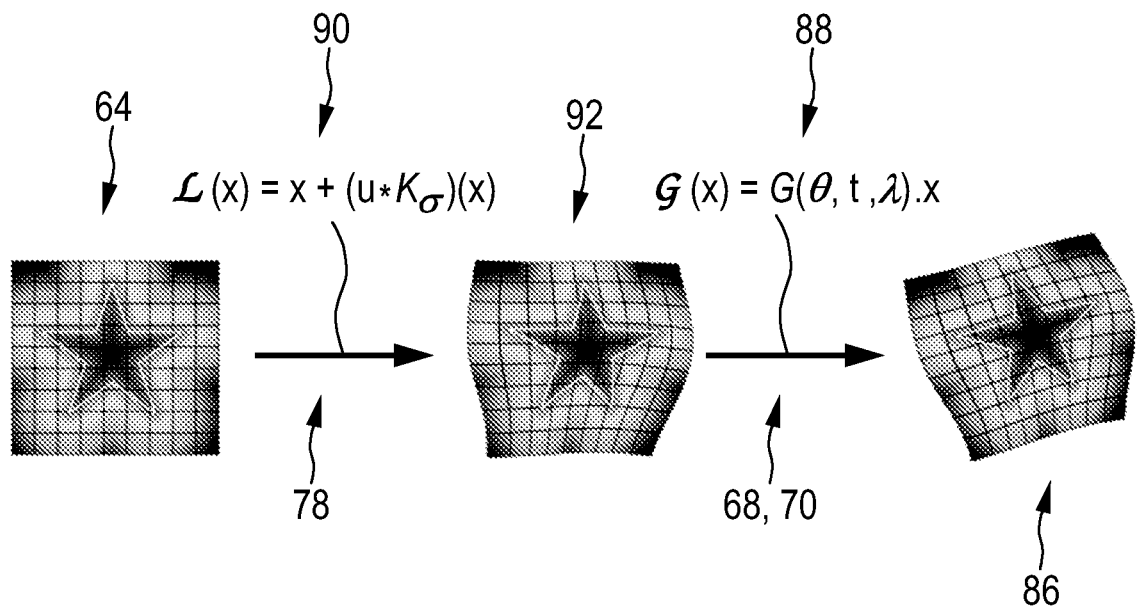

In FIG. 5c, it is, again, shown in detail how the transformation from the initial geometric shape 64 to the deformed model 86 is split up between the local deformation 78 and the global deformation 68, 70. As explained above, a local transformation function 90 is provided that locally deforms the initial geometric shape into a deformed shape 92. Then, a global transformation function 88 is supplied to translate, rotate and scale the deformed shape 92.

Figure 6:
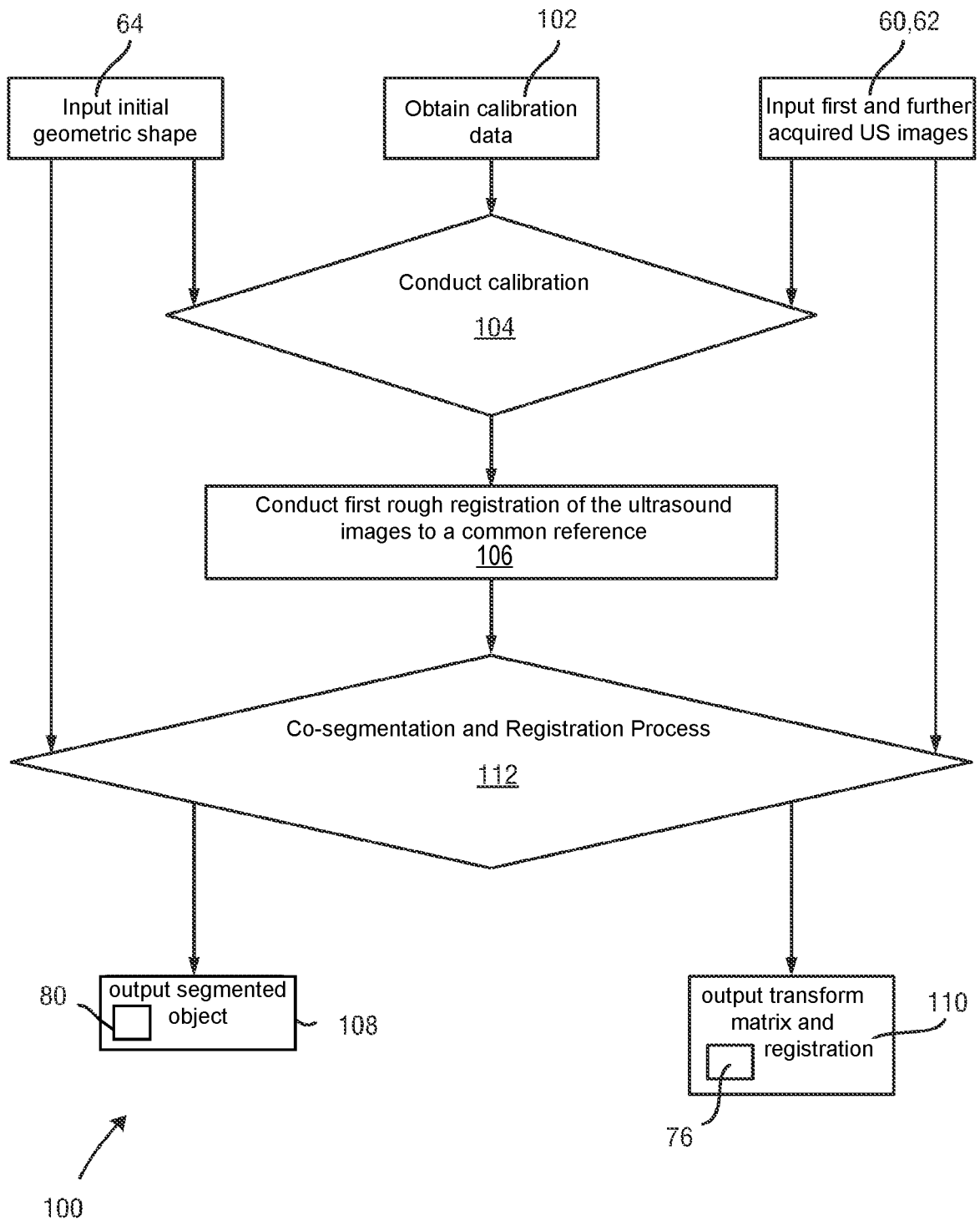
FIG. 6 shows a further block diagram illustrating an embodiment of the whole image acquisition process.

FIG. 6 shows a flow diagram illustrating how the co-segmentation and registration process shown in FIG. 4 is embedded into the improved initialization and calibration according to the current invention. The process shown in FIG. 4 is also present in FIG. 6 as a single block designated with reference numeral 112. The initial geometric shape 64 which in case of the target object 33 being a liver, for example is a mean shape of a liver is inputted into the co-segmentation and registration process 112 as well as the first and further acquired ultrasound images 60, 62. However, to initialize the co-segmentation and registration process, an acquisition protocol is conducted. First, in block 102, calibration data is obtained as will be explained in more detail below with reference to FIG. 7. There, the ultrasound probe is moved to predefined locations on the patient's body in certain positions. By this, the tracking device 25, 27 is initialized. Of course, other ways of initialization could be provided, for example, it could be sufficient to merely acquire a single midline transverse acquisition to calibrate the tracking device. Further, an acquisition protocol could be used, for example guiding various acquisitions according to known viewpoints on the human body, for example mid sagittal, mid axillary coronal, etc.

Then, a calibration is conducted in block 104. A plurality of ultrasound images is acquired via the probe that is provided with the tracking device. At least two acquisitions are made from two different viewpoints. Preferably, acquisitions are made at identical respiration phases. For each image acquisition, the viewpoints are recorded via the tracking device. Then, a first rough registration of the ultrasound images to a common reference is conducted 106. This takes into account the initial geometric shape, the calibration indicating the cranio-caudal axis of the patient or any other defined view in the patient's body and the images and the corresponding viewpoint coordinates. By this, it is possible to roughly register all ultrasound views with a mere translational transformation matrix by using the data of the tracking device. Now, the geometric shape of the object and the rough estimate for the viewpoint position can be input in the co-segmentation and registration process as explained above. As a rough registration is already conducted, the registration search space for the optimum solution can be reduced significantly leading to quicker and more accurate results.

The process as explained together with FIG. 4 then outputs an accurate shape of the segmented object 108 and an accurate transform matrix and registration 110 that leads to exact viewpoint positions of each ultrasound image.

Figure 7:
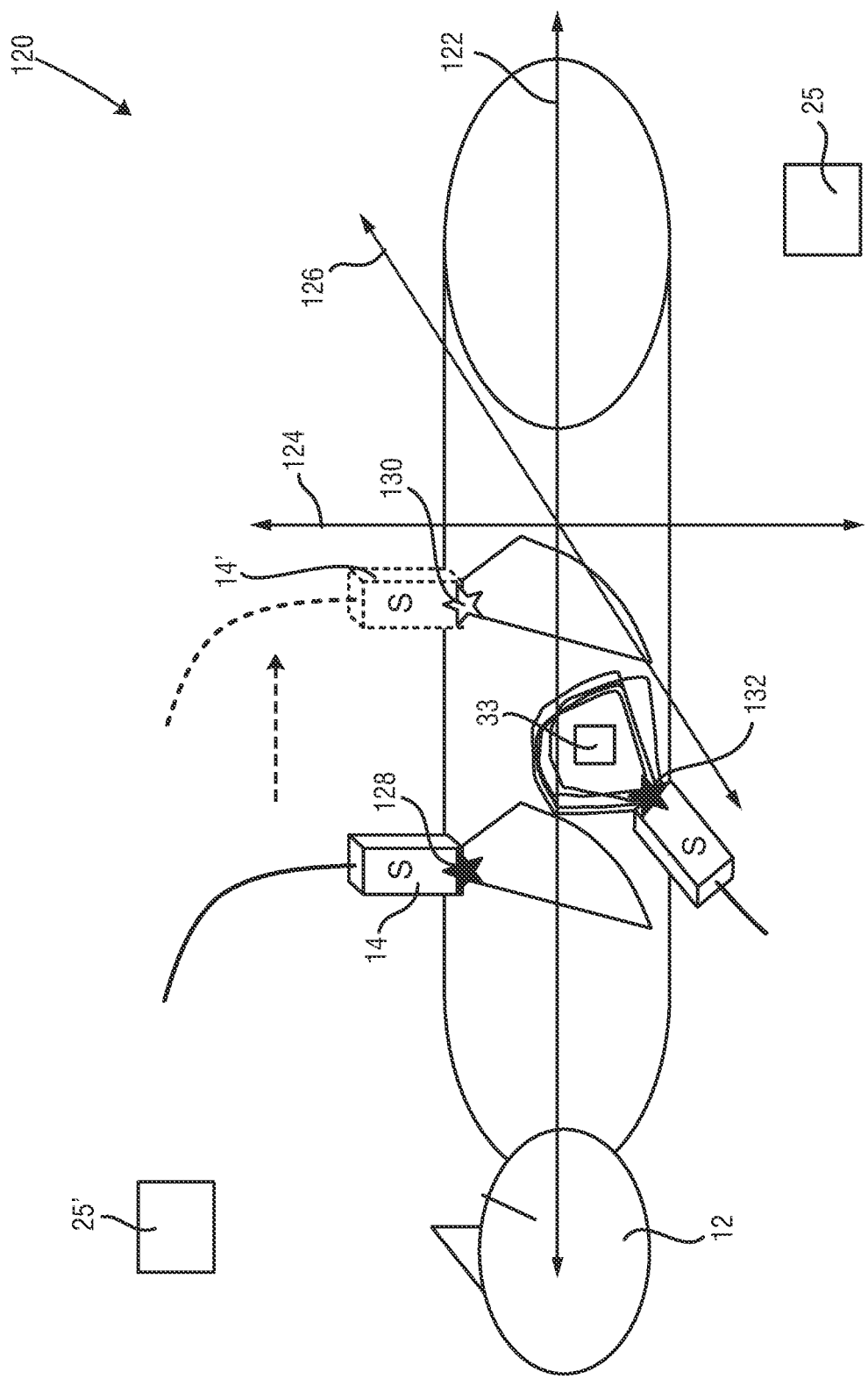
FIG. 7 shows a new schematic illustration of relevant axis and positions on a patient during image acquisition.

FIG. 7 shows a schematic illustration of the body of a patient 12. Rough overview over a possible calibration process 120 is given. The cranio-caudal axis is designated with reference numeral 122. The anterior-posterior axis is designated with reference numeral 124. The left-right axis is designated with reference numeral 126. During the calibration 102, the user moves the probe to a first position 128 and then to a second position 130 on the patient's sternum. No image acquisition needs to be made during this, however, a first initialization of the tracking device, in particular an electromagnetic tracking device 25, 27 is conducted. Alternatively, image acquisition could already be conducted and the images be used subsequently. After this, the image acquisition of the object 33 can take place as usual and the object is scanned via the ultrasound image acquisition probe 14 at a normal acquisition position 132.

Figure 8:
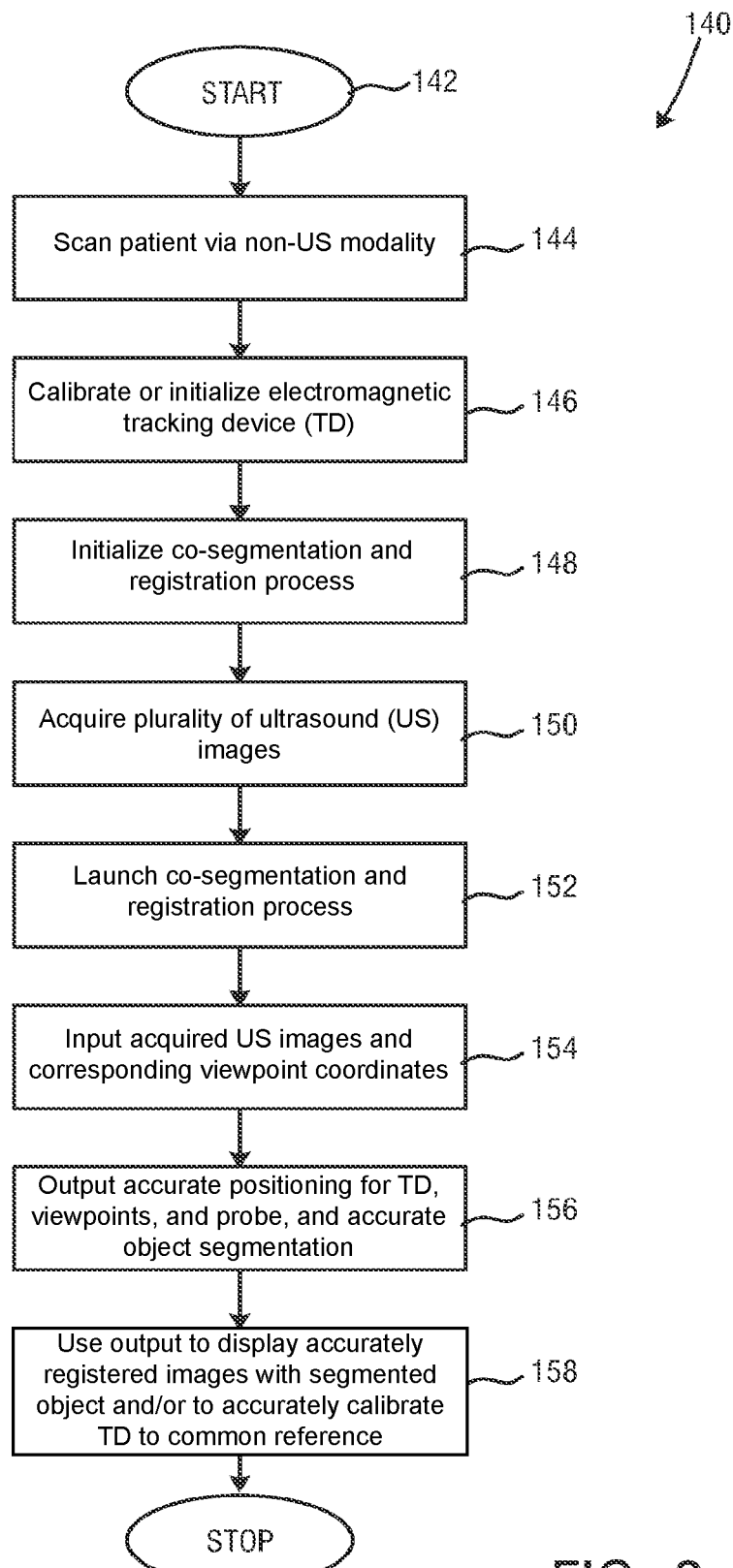
FIG. 8 shows a block diagram of an embodiment of the method.

An embodiment of a method will now be described with reference to FIG. 8 that shows a flow diagram of a method 140. The method will be explained in connection with FIGS. 9a to 9d, that show images acquired during the different steps of the method.

The method starts in a step 142. Then, in a step 144, the patient may be scanned via a different modality. In the current example, it shall be assumed that the purpose is to examine the liver of a patient. Hence, in step 144, the patient's liver is scanned via a computer tomography system. The liver is segmented out of the CT data. The shape of the segmented liver out of the CT images is specified that may form the initial geometric shape that is used later on the co-segmentation and registration process of the ultrasound images. However, the step 144 is merely optional. It may also be possible to choose a basic geometric shape, for example a sphere or a cylinder, as the initial geometric shape.

Some time after the CT examination, for example one or a couple of weeks, it may be the case that the patient is examined via an ultrasound imaging system, for example during a minimally invasive intervention. The ultrasound system used is one according to the current disclosure and is equipped with a tracking device, in particular the ultrasound image acquisition probe is equipped with an electromagnetic tracking device. The patient lies within the electromagnetic field of the electromagnetic tracking device.

Now, in step 146, a first calibration or initialization of the electromagnetic tracking device is conducted. During this, no image acquisition needs to takes place. As explained in connection with FIG. 7, two defined different positions 128 and 130 are touched with the ultrasound image acquisition probe. As the positions are well-defined, the cranio-caudal axis of the patient is initialized in the electromagnetic tracking device. This initialization is also provided to the co-segmentation and registration process.

Figure 9A:
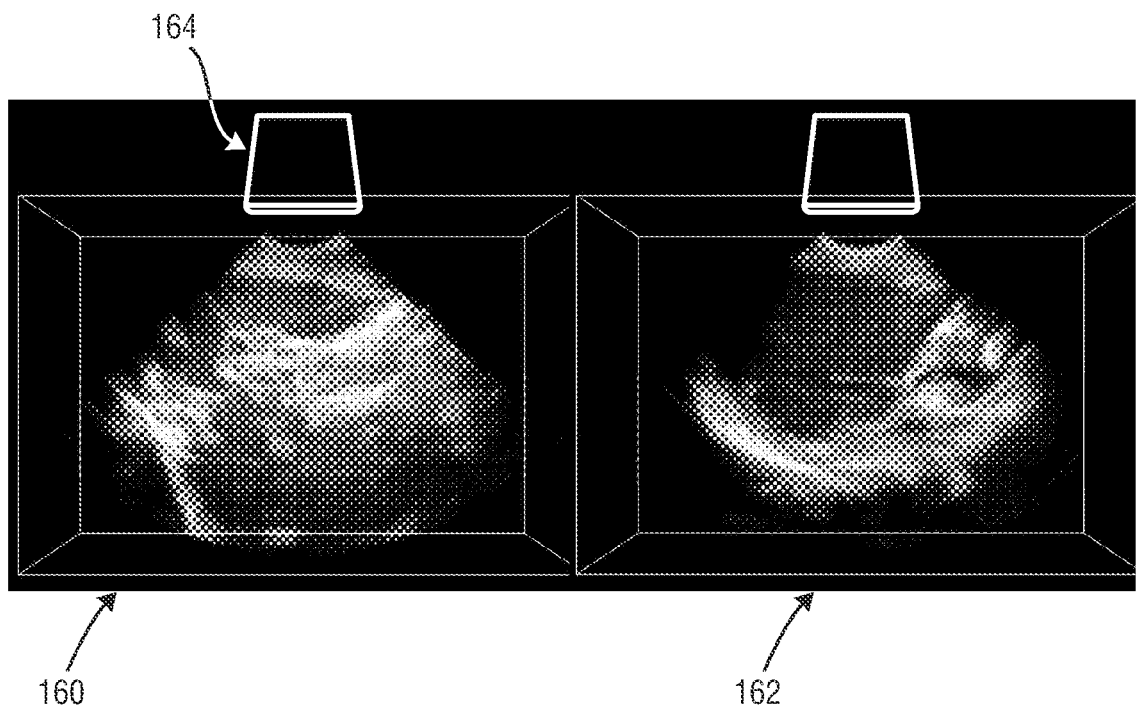
FIGS. 9*a* to 9*d* show image examples to explain the ongoing image acquisition.

Then, an initialization process 148 for the co-segmentation and registration process is conducted. In this, in a step 150, the plurality of ultrasound images is acquired. For each position, the viewpoint coordinates are recorded via the electromagnetic tracking device. The patient may breathe freely, but acquisitions are preferably made at identical respiration phases. For example, two ultrasound acquisitions may be made from two different viewpoints, as illustrated in FIG. 9a. There, a first ultrasound acquisition 160 and a second ultrasound acquisition 162 are shown. A view indicator 164 for orientation reasons is also shown.

Then, in a step 152, the co-segmentation and registration process is launched as it was explained in detail with reference to FIG. 4. In this process, the liver shape acquired via the CT scan may be taken into account as the initial geometric shape 64 by the process. Further, the positions 128 and 130 are provided as an indication of the craniocaudal axis of the patient and all acquired ultrasound images and their corresponding viewpoints coordinates recorded via the electromagnetic tracking device are input 154. The output of the process provides accurate positioning for the electromagnetic tracking device, i.e. the ultrasound image acquisition probe and its electromagnetic tracker, for each viewpoint, further, hence, each probe position relative to a common reference, for example the CT scan and, finally, an accurate liver segmentation in all ultrasound acquisitions 156.

The output of the algorithm may then be used to display accurately registered images with the segmented object, e.g. the liver. Further, as the accurate position of the probe is known, the output of the algorithm may also be used to accurately calibrate the electromagnetic tracking device to the common reference 158.

Figure 9B:
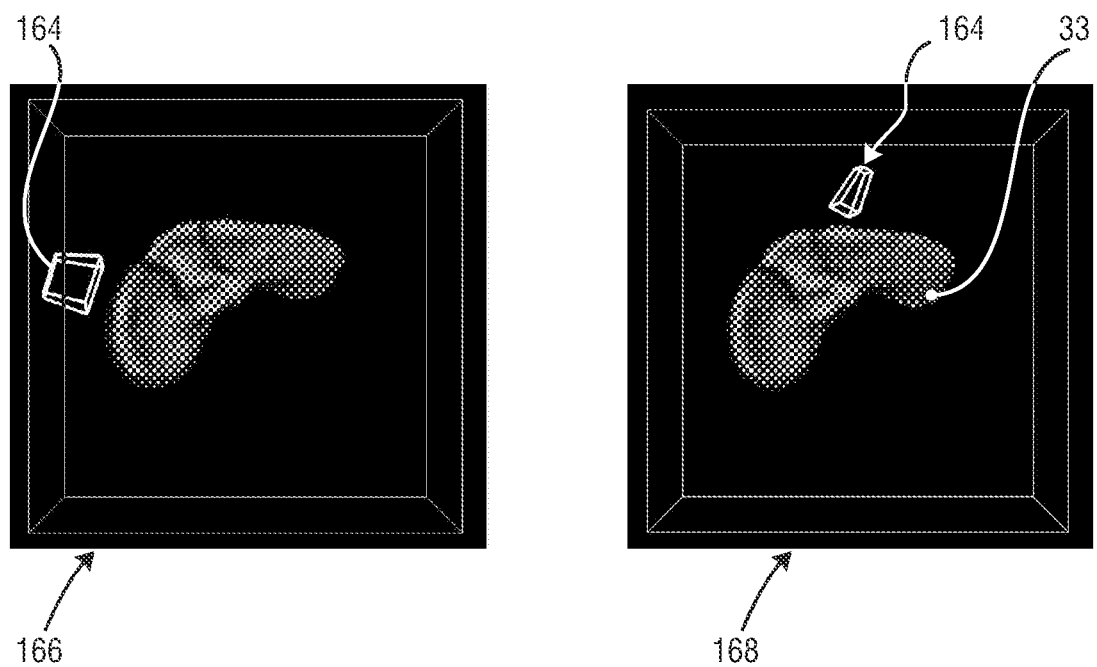
Figure 9C:
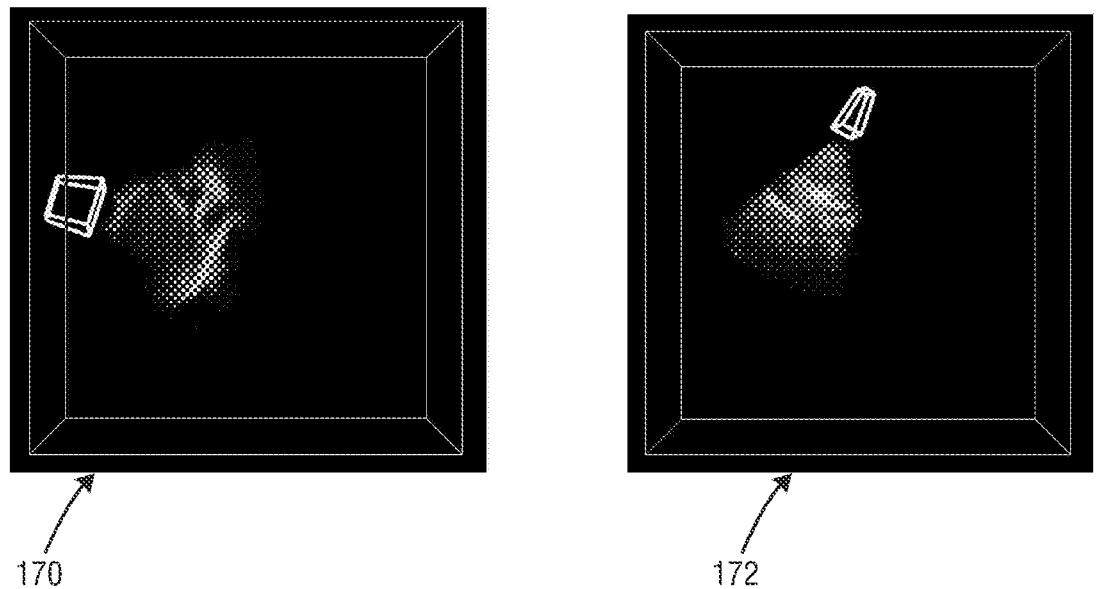

FIG. 9b shows estimated probe positions based the input of the electromagnetic tracking device into the co-segmentation and registration process. The view indicators 164 illustrate the viewpoint of the ultrasound image acquisition probe 14 relative to the segmented liver acquired via the CT scan. As depicted in FIG. 9c, the image acquired via ultrasound acquisition may then be registered with the CT view and displayed correspondingly as shown in FIG. 9c. FIG. 9c shows aligned ultrasound images 170, 172 registered to the CT scan.

Figure 9D:
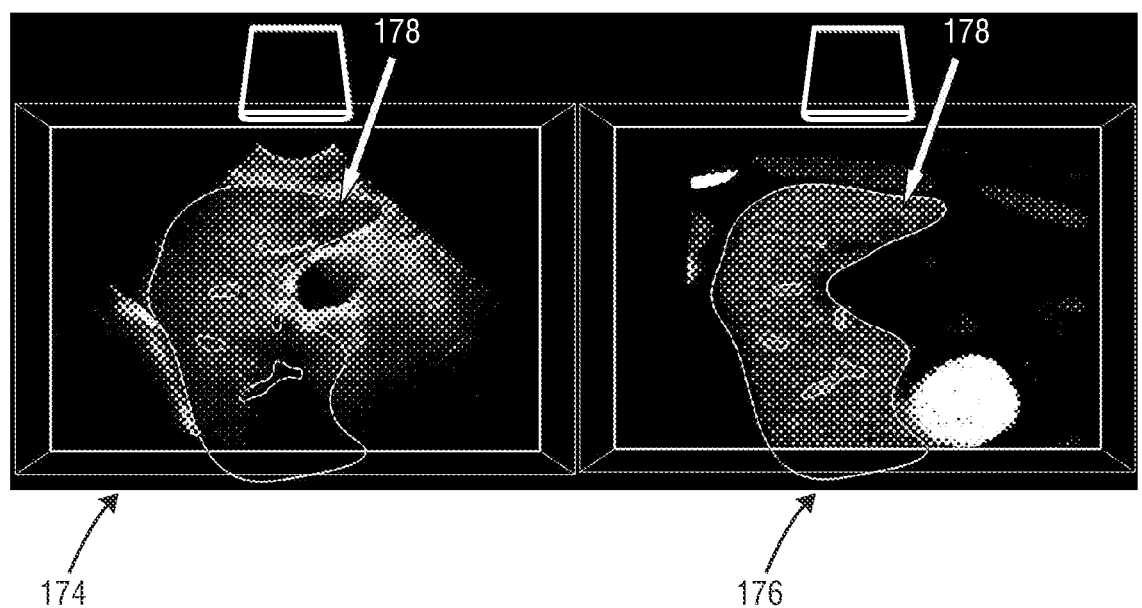

FIG. 9d shows then a further possibility how the output of the process of co-segmentation and registration use. Image 174 shows an ultrasound scan in which the segmented liver is highlighted. Image 176 shows the CT scan also with the segmented liver highlighted. A lesion within the liver that may be searched for is indicated via an arrow 178 and can be localized in the ultrasound scan.

A further example of use may be that the ultrasound scan or a minimally invasive intervention is pursued. For each new ultrasound acquisition, the already segmented liver shape may be superimposed on the ultrasound image. Further, in particular as the electromagnetic tracking device is now properly calibrated and initialized, the data of delivered and recorded by the electromagnetic tracking device can be used to very accurately display a registered ultrasound image life and during use. Further, it is always possible to provide corresponding CT view in parallel.

During intervention, in case visual mismatches between the CT and the ultrasound views or between different ultrasound views shall occur, for example due to a drift in the electromagnetic tracking device, the co-segmentation and registration process may be launched as a "refinement" of the calibration and alignment. Again, a plurality of ultrasound images is acquired from different viewpoints. The co-segmentation and registration process may be launched again using this new captured image data. However, as a system only drifted, the system may be considered as already initialized. Hence, there would be no need for a pre-calibration workflow as explained in step 146 and together with FIG. 7.

The particular embodiment of the invention has been described in field of calibration and on request refinement of an electromagnetic tracker during minimally invasive intervention. Hence, an ultrasound image system equipped with a locating sensor, for example a tracker of an electromagnetic tracking device, benefits from this invention. For the particular embodiment described above, the shape of the liver in CT is accurate. However, the invention also addresses the co-segmentation and registration of a target object for which only a rough estimate of the shape of the object is given, for example a mean shape. So the invention finds its application as well for ultrasound systems only that are equipped with a tracking device and for which no CT scan is available. For this application, the invention then may serve to segment the object within multiple ultrasound views. Further, the co-segmentation and registration may be conducted and supported by MR data and with a plurality of ultrasound views. Hence, also multimodality workstations may have benefits from this invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system for inspecting an object in a volume, the ultrasound imaging system comprising:
    an ultrasound image acquisition probe for acquiring three-dimensional ultrasound images of a volume, wherein the ultrasound image acquisition probe comprises a tracking device for tracking a position of the ultrasound image acquisition probe and providing respective viewpoint positions of the three-dimensional ultrasound images, and
    an image processor configured to:
        receive a plurality of three-dimensional ultrasound images and the respective viewpoint positions of the plurality of three-dimensional ultrasound images;
        simultaneously segment an object out of the plurality of three-dimensional ultrasound images by minimizing an energy term of a space transformation of the object, wherein the energy term is a function of a regularization of the space transformation;
        register, concurrently with segmenting the object, the plurality of three-dimensional ultrasound images with one another; and
        provide display data corresponding to an image of the three-dimensional ultrasound images aligned based on segmenting the object and registering the plurality of three-dimensional ultrasound images.

2. The ultrasound imaging system of claim 1, wherein the energy term comprises a first term representing a first three-dimensional ultrasound image from the plurality of three-dimensional ultrasound images and at least one further term representing a further three-dimensional ultrasound image from the plurality of three-dimensional ultrasound images, and wherein segmentation of the object further comprises deforming an initial geometric shape such that a deformed initial geometric shape matches a shape of the object, the deformed initial geometric shape being the same in both the first and the at least one further term, wherein deforming the initial geometric shape to the deformed initial geometric shape is defined by the space transformation.

3. The ultrasound imaging system of claim 2, wherein a deformation of the initial geometric shape is conducted by applying a global transformation and a non-rigid local transformation on the initial geometric shape, and wherein the non-rigid local transformation applies a displacement field on the initial geometric shape, wherein a dot product of the global transformation and the non-rigid local transformation define the space transformation.

4. The ultrasound imaging system of claim 3, wherein the applying a global transformation includes at least one of translating, rotating, and scaling the initial geometric shape, and wherein the applying a non-rigid local transformation includes applying a displacement field on the initial geometric shape.

5. The ultrasound imaging system of claim 2, wherein the image processor is configured to determine the initial geometric shape based on a segmentation of the object in three-dimensional image data acquired via a modality other than ultrasound.

6. The ultrasound imaging system of claim 5, wherein the modality is computer tomography.

7. The ultrasound imaging system of claim 2, wherein the image processor is configured to receive the initial geometric shape responsive to user input.

8. The ultrasound imaging system of claim 2, wherein at least one of the first and the at least one further term comprises a registering transformation registering the three-dimensional ultrasound image and the at least one further three-dimensional ultrasound image to a common frame of reference.

9. The ultrasound imaging system of claim 8, wherein the common frame of reference system is defined, at least in part, by a coordinate system associated with one of the initial geometric shape, at least one of the plurality of three-dimensional ultrasound images, or image data obtained from a modality other than an ultrasound.

10. The ultrasound imaging system of claim 1, wherein the image processor is further configured to segment the object by initializing a registration search space, the initializing including positioning an initial geometric shape in each of the plurality of three-dimensional ultrasound images.

11. The ultrasound imaging system of claim 10, wherein the image processor is further configured to register the three dimensional-images to each other by optimizing a three-dimensional translation transformation while taking into account a viewpoint position of the ultrasound image acquisition probe when acquiring a respective three-dimensional image.

12. The ultrasound imaging system of claim 10, wherein the ultrasound imaging system is further configured to refine segmentation and registering transformation performed with respect to the plurality of images by segmenting the object out of another plurality of three-dimensional ultrasound images acquired via the ultrasound image acquisition probe.

13. The ultrasound imaging system of claim 1, wherein the tracking device is an electromagnetic tracking device.

14. A method for providing an ultrasound image of an object in a volume, the method comprising:
    providing ultrasound image data comprising a plurality of three-dimensional ultrasound images of the volume and viewpoint positions of each three-dimensional ultrasound image of the plurality of three-dimensional ultrasound images,
    processing the ultrasound image data to:
        segment the object out of a first ultrasound image of the plurality of three-dimensional ultrasound images, and simultaneously segment the object out of at least one further ultrasound image of the plurality of three-dimensional ultrasound images, by selecting an initial geometric shape approximate in shape to the object, deforming, based on a space transformation, the initial geometric shape to match a shape of the object, wherein an energy term of the space transformation is minimized, wherein the energy term is a function of a regularization of the space transformation, and
        concurrently, in parallel with segmenting the object out of the first ultrasound image and the further ultrasound image, register the first ultrasound image with the further ultrasound image to produce a segmented and registered ultrasound image, and
    displaying the segmented and registered ultrasound image.

15. The method of claim 14, further comprising inputting a three-dimensional image of the object acquired using a modality other than ultrasound, wherein the three-dimensional image of the object is used as a reference image during registration of the first ultrasound image and the further ultrasound image.

16. The method of claim 15, further comprising calibrating a tracking device for acquiring the viewpoint positions by moving an image acquisition probe coupled to the tracking device to at least two different locations on a known axis of a patient or orienting the image acquisition probe in a predefined relationship to the known axis.

17. A non-transitory computer-readable medium comprising computer-executable instructions for causing a computer including a display to carry out the steps of the method as claimed in claim 14 when said computer-executable-instructions are carried out on the computer.

* * * * *